United States Patent [19]

Schomburg et al.

[11] Patent Number: 5,114,550

[45] Date of Patent: May 19, 1992

[54] METHOD FOR THE PRODUCTION OF GEL FILLED CAPILLARIES FOR CAPILLARY GEL ELECTROPHORESIS

[75] Inventors: Gerhard Schomburg; Jurgen A. Lux, both of Mülheim/Ruhr, Fed. Rep. of Germany

[73] Assignee: Studiengesellschaft Kohle MbH, Mulhelm A.D. Ruhr, Fed. Rep. of Germany

[21] Appl. No.: 694,742

[22] Filed: May 2, 1991

[30] Foreign Application Priority Data

May 5, 1990 [EP] European Pat. Off. ......... 90108487.1

[51] Int. Cl.⁵ ..................... G01N 27/26; B21D 57/12
[52] U.S. Cl. ................... 204/180.1; 204/299 R; 204/182.8
[58] Field of Search .............. 204/299 R, 182.8, 180.1

[56] References Cited

U.S. PATENT DOCUMENTS

| 4,189,370 | 2/1980 | Boschetti ......................... 204/299 R |
| 4,704,198 | 11/1987 | Ebersole et al. ................. 204/182.8 |
| 4,840,756 | 6/1989 | Ebersole et al. ..................... 264/22 |
| 4,863,647 | 9/1989 | Baylor, Jr. ...................... 264/41 X |

OTHER PUBLICATIONS

Lux, Juergen A; Yin, Hong Feng; Schomburg, Gerhard "A Simple Method for the Production of Gel-Filled Capillaries for Capillary Gel Electro-Phoresis", J. High Resolution Chromatography, 13(6) [1990], 436-437.

Primary Examiner—John Niebling
Assistant Examiner—John S. Starsiak, Jr.
Attorney, Agent, or Firm—Sprung Horn Kramer & Woods

[57] ABSTRACT

The γ-radiation initiated formation of a polyacrylamide gel for the simplified production of gel filled fused silica capillaries for capiliary gel electrophoresis. The performance and stability of such gel filled capillaries are as good as of those obtained by methods known in the art.

9 Claims, No Drawings

METHOD FOR THE PRODUCTION OF GEL FILLED CAPILLARIES FOR CAPILLARY GEL ELECTROPHORESIS

BACKGROUND OF THE INVENTION

The invention relates to the production of capillaries for gel electrophoretic (CGE) separations. In particular, narrow bore fused silica capillaries are filled with a solution of a polymerizable material. The material is polymerized within the capillary by radicals generated by γ-radiation, preferably originated from a $^{60}$Co-source.

Capillary gel electrophoresis as a powerful separation technique especially for the rapid separation of oligonucleotides has been introduced by Karger et al., A. S. Cohen, D. R. Najarian, A. Paulus, A. Guttman, J. A. Smith, B. L. Karger, Proc. Natl. Acad, Sci, USA 85 (1988) 9660, EP-A 0 324 539 and U.S. Pat. No. 4,865,706.

Conventionally gel filled capillaries are produced by a method using radical initiators, such as ammonium persulfate and TEMED (N,N,N',N'-tetramethyleneethylene diamine), as stabilizing agent. Such capillaries may possibly contain highly charged by-products and residual amine which should be removed before use or storage.

SUMMARY OF THE INVENTION

It is an object of the invention to avoid the disadvantages of the prior art, viz non-uniform distribution of the polymer and the presence of impurities due to the incorporation of radical initiators.

In accordance with the present invention there is provided a process for the production of filled capillaries, wherein a microcapillary is filled with a degassed monomer solution and then subjected to γ-radiation of the filled capillary, thereby to form a hydrophilic polymer-containing gel matrix due to polymerization, i.e. linear polymerization or polymerization and crosslinking of the polymerizable material and/or functional reactive compound(s).

In a preferred embodiment the novel process comprises a) degassing a monomer solution containing an acrylamide and/or bisacrylamide mixture in a known solution and buffer, b) by means of a standard filling procedure such as is used for the production of capillary columns in gas chromatography, introducing the solution into a fused silica capillary, c) closing both ends of the capillary and d) exposing the capillary to γ-radiation, thereby to effect polymerization, i.e. linear polymerization or polymerization and crosslinking of the acrylamide and/or bisacrylamide.

No other chemicals such as radical initiators and stabilizers have to be added for the optimal execution of the polymerization.

Such gel filled capillaries permit CGE separations, e.g. of oligonucleotides, at high resolution and with good peak symmetry. The columns are stable and maintain their performance over series of measurements and storage.

Specific functional reactive compounds for the use as connecting materials between the surface of the capillary and the gel, in particular bifunctional reagents, are disclosed in EP-A 0 324 539, viz. 3-methacryloxypropyltrimethoxysilane, -ethoxysilane, vinyltriacetoxysilane, vinyltri(β-methoxyethoxy)silane, vinylchlorosilane and methylvinyldichlorosilane.

The crosslinking agents are selected from the group consisting of N,N'-methylenebisacrylamide, N,N'-(1,2-dihydroxyethylene)-bisacrylamide, N,N'-dialkyltartratediamide, N,N'-crystaminebisacrylamide and N-acryloyltris(hydroxymethyl)aminomethane. Gels to be used are in principle known from EPA 0 324 539.

The invention is directed in particular to a procedure by which series of capillaries can easily and rapidly be produced. Untimely external or internal polymerization of the acrylamides is avoided in this procedure. Moreover, no other chemicals than the acrylamide and/or bisacrylamide mixture dissolved in buffer are needed to provide crosslinked polyacrylamide gels well suited for CGE separations. The polymerization preferably is performed at room temperature and no pressure has to be applied to the fused silica capillary. These moderate conditions of the polymerization reaction in combination with a stretched arrangement for the capillary in front of the radiation source (initiation of the polymerization by a dose gradient of the radiation) avoid the formation of bubbles in the gels within the capillary.

In one preferred embodiment the invention includes producing a detection window near the outlet of the fused silica capillary for in-column UV-detection, by partial burn-off of a narrow section of the polyamide coating.

In a further embodiment of the present invention septa used for instance for the closures of both capillary ends are made of silicon rubber to prevent solvent evaporation during the subsequent polymerization step.

The preferred buffers according to the present invention are tris base, boric acid, urea and other similar buffers.

Although the polymerization and crosslinking of the acrylamide and/or bisacrylamide by γ-radiation is not critical with respect to the specific dose, it is preferred that the γ-radiation originates from a $^{60}$Co-source at a dose from 20 krad to 400 krad. The specific dose will be adjusted to produce gels of the desired performance. The thus-obtained gel filled capillary can then be installed in known or specially built instruments.

In particular, the novel gel filled capillaries, which can be made for example of silica-based material, alumina, beryllia or Teflon, can be used for the separation of oligonucleotides.

The invention will be further description in the following illustrative example.

EXAMPLE

The capillary was filled with a commercially available mixture of acrylamide and bisacrylamide purchased although the same results have been obtained with acrylamide mixtures which have been prepared by applicants with different ratios of the components. The acrylamide stock solution contained 19 g acrylamide and 1.0 g bisacrylamide, diluted to 50 ml with triply distilled water. The components of the buffer were 1.211 g Tris base (Sigma), 1.546 g boric acid (Aldrich) and 42.04 g urea (Fluka) and were dissolved in triply distilled and degassed water and diluted to 100 ml. Samples of oligodeoxycytidine (24–36 mer Sigma) were dissolved in this buffer.

INSTRUMENTATION

Capillary gel electrophoretic separations were performed in a modular instrument consisting of a Spectra Physics UV-detector with a capillary holder equipped with a ball lens, as well as the usual grounding and sampling devices which also contained the electrodes. Into the latter a high voltage platinum electrode was integrated. For safety reasons all devices were machined of nonmetallic materials, in particular an acrylic ester glass, PTFE or polyethylene, and the operator was protected against high voltage by an interlock system. A Vax 3100 work station operated a HCN 35-35000 high voltage power supply (FuG, osenheim, FRG) via an optically decoupled FuG Probus III interface and allowed voltage control for electromigrative sample introduction as well as the adjustment of the actual separation voltage. Separations were performed in fused silica capillaries (100 μm o.d., Polymicro Technologies) of 45 cm effective and 60 cm total length. For in-column detection a 1 mm section of the polyamide coating was removed to form a window at a distance of 45 cm from the injection end of the capillary by burning.

| Sample | 0.1 mg/ml pd(C)$_{24-36}$ |
|---|---|
| Capillary | 45 cm effective, 60 cm total length; 100 μm i.d. polyacrylamide gel filled (6% T, 3% C) |
| Buffer | 0.1M Tris, 0.25M borate buffer. 7M urea: pH 7.5 |
| Injection | electrokinetic: 5000 V 6 s |
| Separation Voltage | 300 V/cm |
| Detection | UV/260 nm |

An electropherogram shows the separation of the mixture of 24 to 36 mer oligonucleotides with excellent resolution and symmetry of peaks as good as those previously published by A. S. Cohen, D. R. Najarian, A. Paulus, A. Guttman, J. A. Smith, B. L. Karger, Proc. Natl. Acad. Sci. USA 85 (1988) 9660 and A. Guttman, A. Paulus, A. S. Cohen, N. Grinberg, B. L. Karger, J. Chromatography 448 (1988) 41.

By contrast, the resolution and the peak symmetries obtained with gel capillaries produced by conventional procedures using ammonium persulfate and TEMED (N,N,N',N'-tetramethyleneethylene diamine) often times deteriorate during storage according to the experience so far.

It will be appreciated that the instant specification and claims are set forth by way of illustration and not limitation, and that various modifications and changes may be made without departing from the spirit and scope of the present invention.

We claim:

1. In the production of a gel filled microcapillary for capillary gel electrophoresis by filling the microcapillary with a solution of a polymerizable monomer and polymerizing the monomer to form a hydrophilic polymer-containing gel matrix, the improvement which comprises effecting the polymerization by γ-radiation of the filled capillary.

2. A process according to claim 1, comprising
   a) degassing a solution of either acrylamide plus bisacrylamide in a buffer of known concentration and ratio of acrylamide/bisacrylamide,
   b) by means of a standard filling procedure as used for the production of capillary columns in gas chromatography, introducing the solution into a capillary,
   c) closing both ends of the capillary, and
   d) exposing the capillary to γ-radiation.

3. A process according to claim 1, wherein the capillary includes a polyamide coating, the process including the further step of generating a detection window near the outlet of the capillary for in-column UV-detection by partially burning-off of a narrow section of the polyamide coating.

4. A process according to claim 1, wherein the buffer comprises Tris-base, boric acid or urea.

5. A process according to claim 1, wherein the polymerization is effected with a $^{60}$Co-source at a dosage from 20 krad to 400 krad.

6. A process according to claim 1, wherein the monomer in the solution is selected from the group consisting of N,N'-methylenebisacrylamide, N,N'-(1,2-dihydroxyethylene)-bisacrylamide, N,N'-dialkyltartratediamide, N,N'-crystaminebis-acrylamide and N-acryloyltris(hydroxymethyl)aminomethane.

7. A gel filled capillary for capillary gel electrophoresis obtained according to the process of claim 1.

8. In a microcapillary gel electrophoresis employing a gel filled capillary, the improvement which comprises employing a capillary produced by the process of claim 1.

9. In the separation of oligonucleotides employing a gel filled capillary, the improvement which comprises employing a capillary produced by the process of claim 1.

* * * * *